United States Patent [19]

Fukushi

[11] 4,454,119

[45] Jun. 12, 1984

[54] THERAPEUTIC AGENTS

[75] Inventor: Kazue Fukushi, Hirosaki, Japan

[73] Assignee: Mitsubishi Chemical Industries Limited, Tokyo, Japan

[21] Appl. No.: 278,712

[22] Filed: Jun. 29, 1981

[51] Int. Cl.³ ............................................. A61K 31/00
[52] U.S. Cl. ..................................................... 424/170
[58] Field of Search ...................... 424/170, 168; 536/1

[56] References Cited

PUBLICATIONS

Frobisher et al., I, "Fundamentals of Microbiology", Saunders Co., Phila., p. 338, 1974.
Frobisher et al., II, "Fundamentals of Microbiology", Saunders Co., Phila., p. 405, 1974.
Rapp, Israel J. Med. Sci., 9, 336–374 (1973).
Bast et al., Annals N.Y. Acad. Sci., 277, 60–93 (1976).
Nowotny, Bacteriological Reviews 33, No. 1, 72–98 (1969).
Milner in Microbial Toxins, vol. IV (1971), Weinbaum et al., pp. 1–65.
Nauts et al., Cancer Research, vol. 6, 205–214 (1946).
Zinsser, Microbiology, 17th Ed. (1980), pp. 496, 497.

*Primary Examiner*—Stanley J. Friedman
*Assistant Examiner*—Rollins, John W.
*Attorney, Agent, or Firm*—Oblon, Fisher, Spivak, McClelland & Maier

[57] ABSTRACT

A therapeutic agent comprising an oil-in-water type suspension of an alkali treated lipopolysaccharide from gram negative bacteria and cord factor of acid fast bacteria or its similar substance of corynebacteria.

14 Claims, No Drawings

THERAPEUTIC AGENTS

BACKGROUND OF THE INVENTION

1. Field of the Invention

The present invention relates to a therapeutic agent, and particularly to a therapeutic agent comprising an oil-in-water type suspension of an alkali treated lipopolysaccharide from gram negative bacteria and a cord factor from acid fast bacteria or its similar substance from corynebacteria.

2. Description of the Prior Art

It has been known that a lipopolysaccharide (hereinafter referred to as LPS) from gram negative bacteria has a therapeutic activity, and many studies have been accumulated demonstrating the effect on the experimental tumor models as well as on the cancer patients. However, LPS itself has not widely been utilized as a drug for clinical treatment due to its strong adverse effect, e.g., pyrogenic activity and endotoxin shock.

SUMMARY OF THE INVENTION

Accordingly, it is an object of the present invention to provide a therapeutic agent containing LPS which is found to have advantageous utility in treating transplanted tumors.

Thus, the present invention provides a therapeutic agent which comprise an oil-in-water type suspension of an alkali treated LPS from gram negative bacteria and a cord factor from acid fast bacteria or its similar substance from corynebacteria.

DETAILED DESCRIPTION OF THE INVENTION

LPS which is used in the present invention is the one derived from the following examples of gram negative rods bacteria:

Escherichia (*E. coli*), Salmonella (*S. minnesota, S. typhimurium, S. enterididis*), Pseudomonas (*P. aeruginosa, P. cepacia, P. maltophilia, P. mallei*), Serratia (*S. marcescens, S. rubudaea*), Proteus (*P. inconstans, P. vulgaris, P. morganii*) Shigella (*S. boydii, S. dysenteriae, S. flexneri*), Brucella, Enterobacter, Klebsiella, Vibrio and the mutants of these bacteria, and derived from the following examples of gram negative cocci: Neisseria (*N. gonorrhoeae, N. meningitidis, N. catarrhalis*), and the mutants of these bacteria.

Among them, *S. minnesota, S. typhimurium, S. marcescens* and *E. coli* are preferred because of the weakness of pathogenic activity. LPS is obtainable from whole cells of these bacteria or preferably from cell walls of these bacteria by the method per se known in the art, for instance;

(1) a phenol-water method (Westphal, O., et al.,: Z. Naturforsch, 73, 148 (1952))

Extraction of glycolipids and lipopolysaccharides with phenol-water (PW)

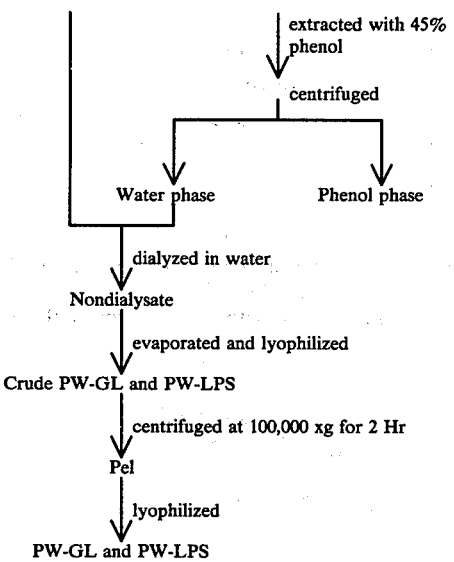

(2) a petroleum ether-chloroform-saturated phenol method (Galanos, C., et al.: Eur. J. Biochem., 9, 245–249 (1969))

Extraction of glycolipids and lipopolysaccharides with saturated phenol-chloroform-petroleum ether (PCP)

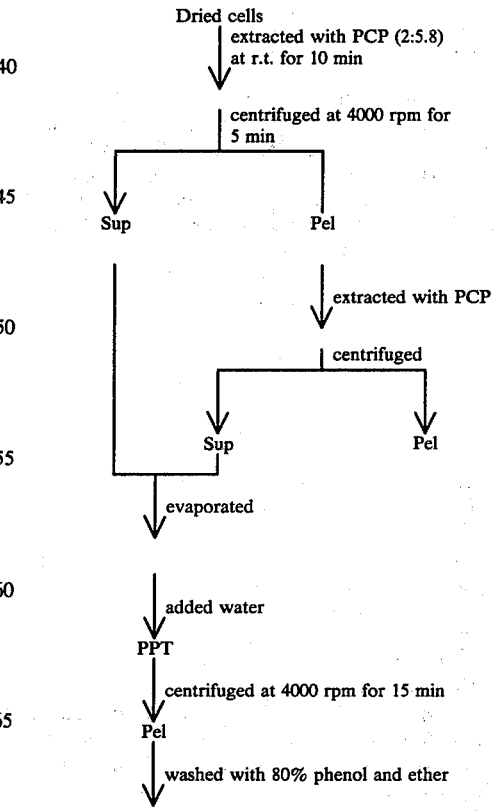

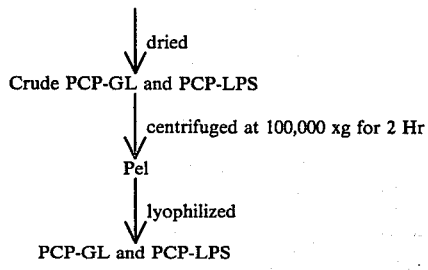

-continued

Crude PCP-GL and PCP-LPS
↓ centrifuged at 100,000 xg for 2 Hr
Pel
↓ lyophilized
PCP-GL and PCP-LPS (3) a chloroform-methanol method (Chen, C. H., et al.: J. Infect. Dis., 128, S43–S51, 1973)

Extraction of glycolipid with chloroform-methanol (CM)

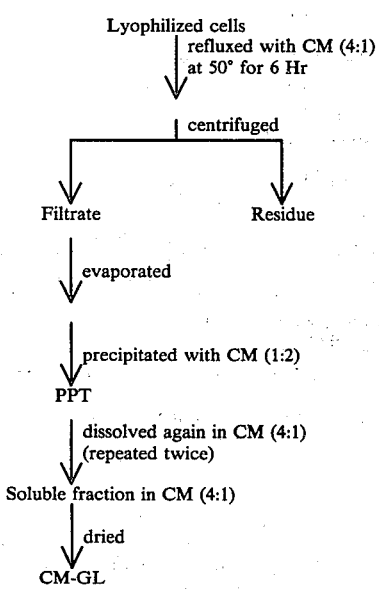

Lyophilized cells
↓ refluxed with CM (4:1) at 50° for 6 Hr
↓ centrifuged
Filtrate    Residue
↓ evaporated
↓ precipitated with CM (1:2)
PPT
↓ dissolved again in CM (4:1) (repeated twice)
Soluble fraction in CM (4:1)
↓ dried
CM-GL In the present invention, LPS extracted by the method mentioned above, purified by e.g. ultracentrifugation is treated by an alkali such as NaOH, NH$_2$OH, ammonia, KOH, alkaline NH$_2$OH or hydrazine. It is considered that a part of the ester-linked fatty acid moiety of lipid A constituting an active center of LPS is removed by this alkaline treatment. The conditions of the alkaline treatment vary with the alkali used, but the general conditions are as follows:

pH 8
Temperature 20°–100° C.
Time 30 sec-several days, preferably one minute to one hour As the pH value or the temperature increases, the time of the treatment decreases.

According to the present invention, the alkali treated LPS is used in combination with the cord factor derived from the acid fast bacteria or its similar substance from corynebacteria. It is known that this cord factor or its similar substance contains trehalose dimycolate as the major component (for instance; Ribi, E., et al.: Microparticulate gel chromatography accelerated by centrifugal force and pressure. In method of Bio-chemical Analysis, New York, John Willey and Sons, 1974, Vol. 22, p355; Auma et al., U.S.-Japan Cooperative Medical Science Program, p398–424 (1977)). This cord factor is obtainable, for instance, by a so-called Noll and Bloch method (Noll, H., and Bloch, H.,: J. Biol. Chem., 214, 251–265, 1955). Exemplary of the acid fast bacteria are Mycobacterium (M. tuberculosis, M. bovis, M. smegmatis, M. kansasii), Nocardia (N. rubra, N. asteroides), and Rhodochrous. Exemplary of the corynebacteria are C. diphtheriae and C. parvum. In the therapeutic agent according to the present invention, the alkali treated LPS and the cord factor or its similar substance are used as an oil-in-water suspension. As the oil, there may be used a mineral oil, a vegetable oil or an animal oil, for instance, a mineral oil such as liquid paraffin; an animal oil such as squalene or squalane; a vegetable oil such as olive oil, peanut oil, sesame oil, safflower oil, corn oil or soybean oil; or vitamine A, vitamine E.

In the preparation of the suspension, the alkali treated LPS and the cord factor or its similar substance are used in proportion of from 20:1 to 1:2, preferably from 6:1 to 1:1, each in weight. The surfactants can be added to the suspension to maintain the stability of oil-in-water suspension. Examples of the suitable surfactants are nonionic surfactants such as polyethylene-glycol alkyl ether, polyethyleneglycol aliphatic acid ester, sorbitan aliphatic acid ester, aliphatic acid monoglyceride. Such surfactants include polyoxyethylene sorbitan monostearate, sorbitan monopalmitate and polyethylene glycol monostearate.

The amount of the oil in the oil-in-water suspension is 0.01–10% in volume, and preferably 0.05 to 5%. The mixture of LPS, cord factor or its similar substance, oil and appropriate surfactant in the physiological aqueous buffer is emulsified by a method such as stirring, vibration, homogenizing or sonication. The therapeutic agent of the present invention may be administered orally or parenterally. However, it is usual to employ an intravenous, intramuscular, intralesional or subcutaneous injection. A dose is determined depending on the age, symptom of the subjects, but for instance, in the case of a subcutaneous injection, a dosage per day is from 0.01 μg to 1 mg of the alkali treated LPS preferably from 0.1 to 100 μg/kg. In the case of oral administration, it is usual that the dosage takes a form of a medicated syrup or an emulsion type internal medicine.

In the therapeutic agent of the present invention, the alkali treated LPS and the cord factor or its similar substance are used in combination as an oil-in-water suspension, and it is thereby possible to substantially reduce the toxicity of LPS and at the same time, it is possible to obtain an excellent therapeutic activity, which is not obtainable when LPS or the cord factor or its similar substance is used independently from each other.

Now, the present invention will be described in more detail with reference to toxicity tests, and pharmacological tests.

EXAMPLE 1

Preparation of Therapeutic Agent (1) Extraction of LPS

LPS of the Salmonella minnesota 1167-R595 (Re) (FERM BP-13) was extracted by the petroleum ether-chloroform-saturated phenol method according to Galanos et al. 50 g of the dried bacteria were placed in a centrifuge vessel and 200 ml of the extraction mixture containing liquid phenol (90 g of dry phenol plus 11 ml of water, chloroform and petroleum ether in a volume ratio of 2:5:8, respectively) was added. The suspension was then homogenized by Ultrasonic Generator KMS-250 (Kubota Seisakusho, Tokyo) for 2 minutes.

The bacteria were then centrifuged off (5,000 rpm, 15 minutes) and the supernatant which contained the LPS was filtered through filter paper into a flask. The bacterial residue was extracted with the same amount of the extraction mixture. Petroleum ether and chloroform were removed completely from the pooled supernatant on a rotary evaporator, whereby phenol crystals remained. Water was added to the dissolved solution until the LPS was precipitated. The precipitate was washed with small portions of 80% phenol. Finally, the precipitate was washed three times with ether to remove any remaining phenol, and dried in vacuo. LPS was taken up in distilled water (50 ml), warmed to about 45° C. and freeze-dried.

(2) Alkali Treatment

LPS obtained by the above method was treated with (i) 0.1N NaOH in ethanol at 37° C. for 30 minutes, or (ii) 2% alkaline (NaOH) $NH_2OH$ in ethanol at 63° C. for 3 minutes, then neutralized with hydrochloric acid, followed by freeze-drying. Chloroform was added to the residue and the insoluble residue was collected and disolved in water and finally freeze-dried.

(3) Extraction of Cord Factor

BCG cord factor was obtained by the following Noll & Bloch method:

ISOLATION OF CORD FACTOR

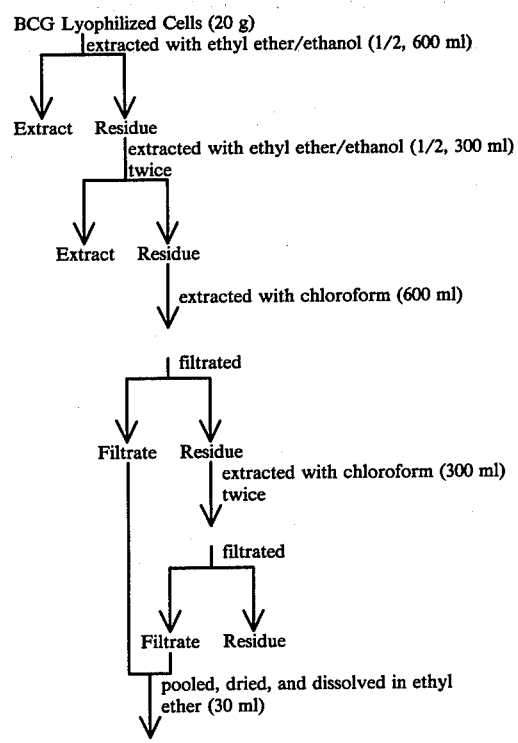

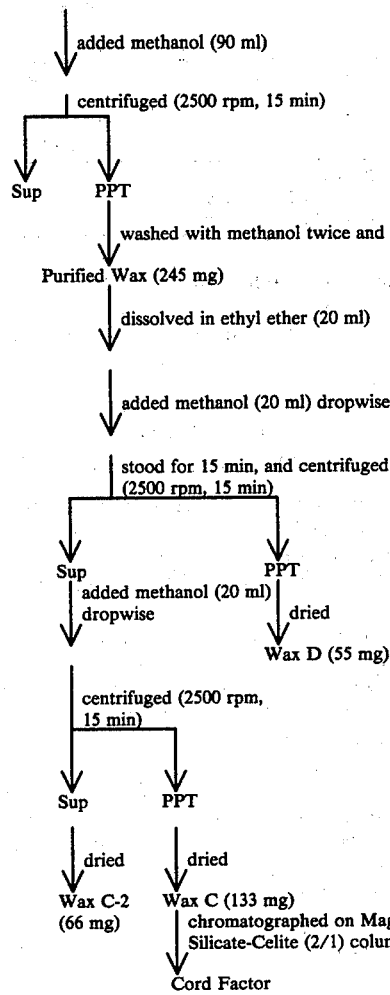

BCG represents the Bacillus of Calmette and Guerin, a bovine strain of tubercle bacillus with a low virulence.

(4) Preparation of Oil-in-water Suspension (therapeutic agent) 2 mg of the alkali treated LPS and 0.5 mg of the cord factor (50 μl of 100 mg/ml of chloroform stored in a deep freezer) were placed in a homogenizer. The homogenizer is placed in a vacuumed desiccator to evaporate chloroform.

20 μl of mineral oil "Violess U-6" (Maruzen Oil Co., Ltd., Tokyo) is then introduced into the homogenizer with use of a micro pipette, and a grinder is inserted and a homogenizing operation was carried out at 800 rpm for 3 minutes.

2 ml of a physiological phosphate buffered sodium chloride solution containing 0.2% of a surfactant (50 mM of Na-phosphate buffer pH 7.4, 0.15M of NaCl, an 0.2% of "Tween 80") was then added.

The mixture was further homogenized at 800 rpm for 3 minutes, and then heated in a hot bath at 65° C. for 30 minutes for sterilization.

EXAMPLE 2

Endotoxic Activity

Endotoxic activity of the extracted LPS and of the alkali treated LPS were determined by the Limulus test (Levin J., Bang F. B., Bull. Johns Hopkins Hosp., 115, 265 (1964)) using Pre Gel. (Seikagaku Kogyo Co., Tokyo).

The results thereby obtained are shown in Table 1.

TABLE 1

Endotoxic Activities of *Salmonella minnesota* Re Lipopolysaccharides

| LPS Type | Endotoxic activity (Limulus Test, µg/ml) |
|---|---|
| Extracted LPS, Example 1(1) | $2 \times 10^{-5}$ |
| 0.1N NaOH treated LPS, Example 1(2) (i) | $2 \times 10^{-1}$ |
| NH$_2$OH treated LPS, Example 1(2) (ii) | 25 |

From the above Table, it is seen that the alkali treated LPS have an extremely reduced toxicity. Especially, in the case of the NH$_2$OH treatment, the toxicity was reduced to less than one millionth of that of an untreated LPS.

EXAMPLE 3

Therapeutic Activity

The ascites form of the diethylnitrosoamine-induced line 10 hepatocellular carcinoma in strain 2 guinea pig (Rapp et al, J. Nat. Cancer Inst., 41, 1–11, 1968) was harvested from the animal. Each guinea pig received an i.d. transplant of $1 \times 10^5$ or $1 \times 10^6$ ascitic line 10 tumor cells in 0.1 ml injected on the flank. 5 to 7-days old tumors were about 10 mm in diameter. To this tumor, the therapeutic agent of the present invention as prepared in Example 1(4) was injected once 5 days after the transplant in an amount of 0.4 ml, and the size of the tumor was measured every day, thus observing the regression of the tumor. There was also injected similarly prepared oil-in-water suspensions of untreated LPS extracted from whole cell and from cell walls combined with the cord factor.

The results thereby obtained are shown in Table 2, as compared with groups of control guinea pigs which were untreated or treated by injection of the vehicle alone.

TABLE 2

Effect of LPS-Cord Factor on Line 10 Tumor Model

| Oil-in-water suspension treatment | $1 \times 10^5$ (A) | | $1 \times 10^6$ (B) | | (A) + (B) | |
|---|---|---|---|---|---|---|
| | No. cured/Total* | % | No. cured/Total | % | No. cured/Total | % |
| LPS (whole cell)**-cord factor | 2/5 | 40 | 10/10 | 100 | 12/15 | 80 |
| LPS (cell wall)***-cord factor | 15/20 | 75 | — | | 15/20 | 75 |
| 0.1N NaOH treated LPS-cord factor | 2/4 | 50 | 1/8 | 12 | 3/12 | 25 |
| NH$_2$OH treated LPS-cord factor | 14/22 | 64 | 7/15 | 47 | 21/37 | 57 |
| Oil-Tween 80-PBS (control) | 0/9 | 0 | 0/13 | 0 | 0/22 | 0 |

*Cured means complete regression of tumor
**LPS extracted from whole cells
***LPS extracted from cell walls The (A)+(B) column reports for each treatment the sum of the total animals cured in colunns (A)+(B) over the total number of animals treated.

Having now fully described the invention, it will be apparent to those ordinally skilled in the art that many changes and modifications can be made thereto without departing from the spirit or scope of the invention as set forth herein.

What is claimed as new and intended to be covered by Letters Patent is:

1. A therapeutic agent comprising an oil-in-water suspension of (A) an alkali treated lipopolysaccharide from gram negative bacteria and (B) a cord factor of acid fast bacteria or its similar substance of corynebacteria, the proportions of (A) to (B) being 20:1 to 1:2 by weight.

2. The therapeutic agent of claim 1, wherein the gram negative bacteria are gram negative rods bacteria.

3. The therapeutic agent of claim 2, wherein the gram negative bacteria are Salmonella.

4. The therapeutic agent of claim 3, wherein the gram negative bacteria are *Salmonella minnesota* or *Salmonella typhimurium*.

5. The therapeutic agent of claim 2, wherein the gram negative bacteria are Serratia.

6. The therapeutic agent of claim 5, wherein the gram negative bacteria are *Serratia marcescens*.

7. The therapeutic agent of claim 2, wherein the gram negative bacteria are Escherichia.

8. The therapeutic agent of claim 7, wherein the gram negative bacteria are *Escherichia coli*.

9. The therapeutic agent of claim 1, wherein the lipopolysaccharide is treated by hydroxylamine or alkaline hydroxylamine.

10. The therapeutic agent of claim 1, wherein the suspension contains the cord factor of the acid fast bacteria.

11. The therapeutic agent of claim 10, wherein the acid fast bacteria are Mycobacterium.

12. The therapeutic agent of claim 11, wherein the acid fast bacteria are selected from the group consisting of *Mycobacterium tuberculosis*, *Mycobacterium bovis* and *Mycobacterium smegmatis*.

13. The therapeutic agent of claim 1, wherein a mineral oil is used to prepare the oil-in-water suspension.

14. The therapeutic agent of claim 13 wherein the proportions of (A) to (B) are 6:1 to 1:1 by weight.

* * * * *